United States Patent [19]

Lubecki et al.

[11] 4,450,576
[45] May 22, 1984

[54] APPARATUS FOR CONTINUOUSLY MEASURING THE ELEMENT CONTENT IN SLURRIES

[75] Inventors: Andrzej Lubecki, Stutensee; Kurt Wiese, Stutensee-Büchig; Karl Winkler, Steinweiler, all of Fed. Rep. of Germany

[73] Assignee: Gesellschaft mit Kernforschungszentrum Karlsruhe beschränkter Haftung, Karlsruhe, Fed. Rep. of Germany

[21] Appl. No.: 360,888

[22] Filed: Mar. 22, 1982

Related U.S. Application Data

[63] Continuation-in-part of Ser. No. 141,698, Apr. 18, 1980, Pat. No. 4,388,530.

[30] Foreign Application Priority Data

Apr. 20, 1979 [DE] Fed. Rep. of Germany ....... 2915986
Mar. 20, 1981 [DE] Fed. Rep. of Germany ....... 3110944
Mar. 21, 1981 [DE] Fed. Rep. of Germany ....... 3111187

[51] Int. Cl.³ ........................ G01N 23/20; G21K 1/00
[52] U.S. Cl. ......................................... 378/47; 378/83
[58] Field of Search ............................. 378/45, 47, 83

[56] References Cited

U.S. PATENT DOCUMENTS 4,152,591 5/1979 Averitt et al. ..................... 378/47

FOREIGN PATENT DOCUMENTS 51-80765 1/1978 Japan ..................................... 378/47

Primary Examiner—Alfred E. Smith
Assistant Examiner—T. N. Grigsby
Attorney, Agent, or Firm—Sughrue, Mion, Zinn, Macpeak & Seas

[57] ABSTRACT

An apparatus for continuously measuring the elemental contents of a slurry independent of the slurry density and slurry composition, by utilizing X-ray fluorescence analysis. The apparatus includes a measuring chamber with a slurry flow channel and a first measuring window disposed on one side of the channel and a second measuring window disposed on the other side of the channel. A first source of primary radiation and a target are disposed behind the second measuring window. A detector is disposed behind the first measuring window. An annular source of primary radiation is provided around an open passage formed by a collimator between the detector and the first measuring window. The collimator collimates the primary radiation and the target radiation as well as the X-ray radiation excited by the first source and the annular source.

6 Claims, 6 Drawing Figures

APPARATUS FOR CONTINUOUSLY MEASURING THE ELEMENT CONTENT IN SLURRIES

CROSS REFERENCE TO RELATED APPLICATION

This application is a continuation-in-part of U.S. patent application Ser. No. 141,698, filed Apr. 18, 1980, now U.S. Pat. No. 4,388,530 which is incorporated herein by reference.

BACKGROUND OF THE INVENTION

The present invention relates to an apparatus for continuously measuring the elemental content of a slurry independently of the slurry density and slurry composition by utilizing X-ray fluorescence analysis.

Due to the rising worldwide need for raw materials, it is increasingly necessary to mine deposits having a low content of the desired raw material. Such deposits are primarily exploited with the use of the flotation method. In the flotation method, valuable mineral is obtained from an aerated suspension of finely ground raw materials and water, a so-called flotation slurry, with the aid of chemicals. Use of this method requires continuous analysis of the product streams to insure economic operation of facilities which often include widely branched-out slurry conduits. Analytical devices are required which quickly indicate the mineral contents of interest at strategically important points in the process to make it possible to quickly intervene in the operation of the process. This is particularly necessary when monitoring the waste streams and the concentrate streams leaving the production facility. Losses of valuable minerals in the waste stream result in considerable financial erosion in the operation of such a facility.

Further, the quality requirements imposed by the processing industry which uses the resultant concentrates are very high and can be met only with difficulty. The industry requirements not only relate to providing concentrates with a specific content of valuable mineral, but also to providing the concentrates with precise proportions of so-called deleterious components. Exceeding such proportions can lead to considerable financial losses and can result in having to discard the entire product.

It is customary to conduct the control of the process streams by means of wet chemical analysis, especially in relatively small flotation plants. This analysis method cannot be effected continuously and requires a considerable amount of time. Using wet analysis it is initially necessary to withdraw samples from the product streams and to process these samples appropriately by drying, grinding, homogenizing, etc., before analysis can begin. Using such wet chemical analysis methods, a time delay of several hours up to a day can be expected from the time the sample is taken to the time the result of analysis is obtained. As a result, entire daily productions, on occasion, may have to be discarded.

Time-consuming wet chemical analysis is being replaced in part by X-ray fluorescence. In this method, dispersive, conventional, multichannel X-ray spectrometers excited by an X-ray tube are used. Although a substantial saving in time is obtained as compared with wet chemical analysis, use of these devices still involves an undesirable time delay between the taking of the sample and the analytical result caused by the necessary preparation of the sample.

Only a continuous, rapid, and highly responsive quality control promotes efficient production by a controlled intervention in the process operation. In order to reduce the time delay occurring between the taking of the sample and the analytical result, devices and processes have been developed which make it possible to carry out a direct analysis at the product stream. In this context, mention is made of the on-stream analysis system Courier 300 developed by the company Outokumpu Oy of Finland. This device is, in principle, a continuously operating sample-taking system with discontinuous analysis based on X-ray fluoresence. In this process, a partial product stream is drawn via pumps and pipelines from various sample taking points in the flotation plant and conducted to a battery of measuring cells. A movable measuring head with X-ray tube and analytical section travels at predetermined time intervals along the various cells and determines in a quasi-continuous fashion the elemental contents of the individual slurry streams. This arrangement, however, is very expensive and it is difficult to financially justify it for use in relatively small flotation plants.

So-called immersion probes have also been developed. In contrast to the conventional X-ray fluorescence method, these devices utilize excitation by an isotope source in place of excitation by an X-ray tube. The immersion probes are hung in the slurry stream. In the case of flotation plants, for example, they are hung in the so-called flotation cells. One disadvantage in this method is the inhomogeneity of the slurry usual in flotation cells. Further, an additional density measuring probe is necessary in all cases. Such immersion probes have been developed by the companies Outokumpu Oy of Finland, Philips of Australia, and NUTMAQ of England.

All of the on-line analysis devices heretofore developed on the basis of X-ray fluorescence initially determine the element content of the slurry. The determination of the element content in the solid matter, however, requires an additional measurement of the slurry density. Because densimeters operate accurately only in a bicomponent system of liquid/solid matter, the measurements can be in error due, for example, to air occlusions which often occur in the slurry in flotation processes. This is a disadvantage of conventional X-ray fluorescence analysis (XRFA) processes.

In addition to the devices operating on the basis of X-ray fluorescence, there are also on-line analysis devices operating according to the principle of neutron activation analysis. In these devices, a partial slurry stream first flows continuously through an irradiation cell with the neutron source. The slurry is "activated" at this point and then flows via an inductive flowmeter into a measuring cell provided with a detector where the induced activity is measured. During blackflow, the slurry passes a densimeter. The required use of the densimeter in the neutron activation analysis process results in the same disadvantages noted above in the X-ray fluorescence analysis process. Furthermore, in the neutron activation analysis process a specific slurry throughflow must be maintained constant at all times.

In our prior filed U.S. patent application, Ser. No. 141,698 now U.S. Pat. No. 4,388,530 we disclose an apparatus utilizing X-ray fluorescence to provide for the rapid and continuous element analysis of a process stream. In that apparatus a measuring chamber with a slurry flow channel is provided at each side with a measuring window. The detector is disposed behind one measuring window and a primary radiation source and a target are disposed behind the other measuring window. The transmitted pimary and target radiation as well as excited X-ray radiation are detected by the detector. This design of the measuring chamber, however, is not sufficient when determining, for example, the content of Pb in the slurry due to the low X-ray yield of Pb in that chamber geometry.

SUMMARY OF THE INVENTION

It is an object of the present invention to provide an apparatus that can be used for analysis of the content of an element in a slurry.

A further object of the present invention is to provide such an apparatus which can be used for analysis of PB in a slurry.

Another object of the present invention is to provide such an apparatus which can be used for analysis of, for example, Pb in PbS/ZnS flotation slurries having varying Pb contents from 0.1% in the total recovery stream up to 84% and more in the Pb concentrate.

Additional objects and advantages of the present invention will be set forth in part in the description which follows and in part will be obvious from the description or can be learned by practice of the invention. The objects and advantages are achieved by means of the apparatus, instrumentalities and combinations particularly pointed out in the appended claims.

To achieve the foregoing objects and in accordance with its purpose, the present invention provides an improved apparatus for the continuous measurement by X-ray fluoescence analysis of the elemental contents of a slurry independent of the slurry density and slurry composition. The improved apparatus includes the basic arrangement of the measuring chamber described in our copending U.S. patent application, Ser. No. 141,698 now U.S. Pat. No. 4,388,530. Thus, the apparatus includes a measuring chamber having a slurry flow channel. The chamber has a first measuring window disposed on one side of the channel and a second measuring window disposed on the other side of the channel. A first primary radiation source and a target are disposed behind the second measuring window and a detector is disposed behind the first measuring window. The first primary radiation source excites the target to emit target radiation and also excites the slurry contents to emit X-ray radiation. The primary radiation from the first source, target radiation and excited X-ray radiation are transmitted to and detected by the detector. In accordance with the improvement of the present invention a collimator means forms an open passage between the detector and the first measuring window, and an annular source of primary radiation for irradiating the slurry contents to excite additional X-ray radiation therefrom is located between the detector and the first measuring window. The collimator means collimates the primary radiation, the target radiation and the X-ray radiation excited by the first primary radiation source and the annular source.

It is to be understood that both the foregoing general description and the following detailed description are exemplary and are not intended to be restrictive of the invention.

DETAILED DESCRIPTION OF THE PREFERRED EMBODIMENTS

The basic concept of the measuring apparatus disclosed in our prior filed, and copending, U.S. patent application, Ser. No. 141,698 now U.S. Pat. No. 4,388,530 has not been changed. A representative partial slurry stream is removed from the product stream and fed to a measuring unit or system such as described in Ser. No. 141,698, now U.S. Pat. No. 4,388,530 by means of a pump. The slurry stream to be analyzed continuously flows through a stirring vessel where it is homogenized. A representative partial slurry stream is removed from the homogenized slurry contained in the stirring vessel and fed by means of a pump through a flow-meter and through a measuring chamber 1 (shown in FIGS. 1 and 2) which is part of and which is firmly screwed to the measuring system in the pump pressure line. The partial slurry stream is returned via an outlet chamber to the stirring vessel or discharged into the main slurry stream.

Figure 1:
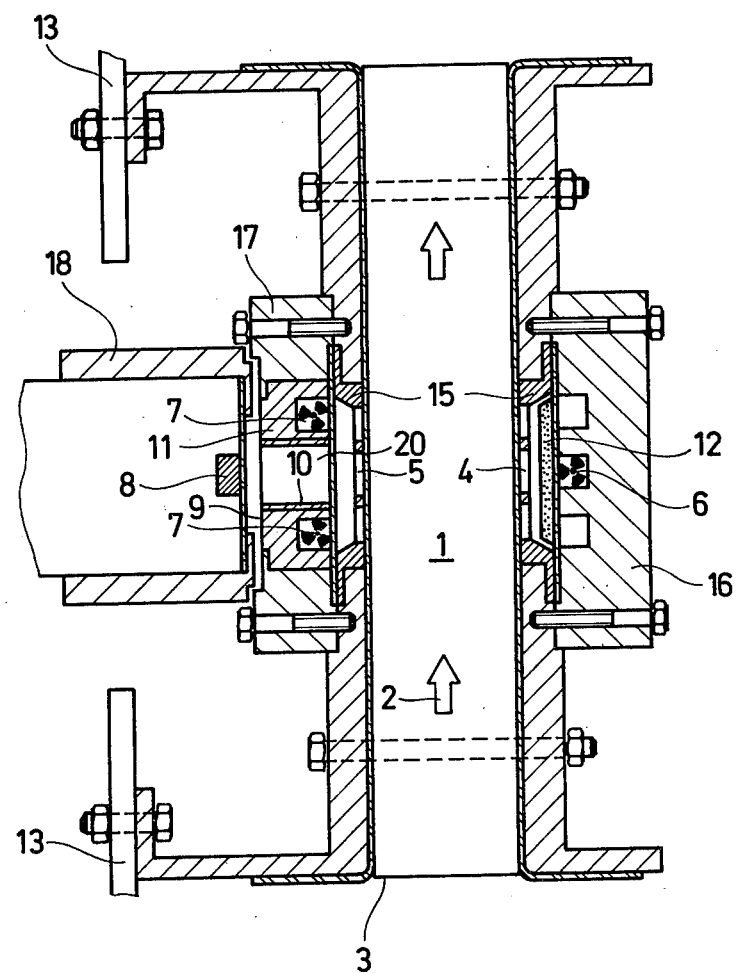
FIGS. 1 and 2 are different sectional views through a measuring chamber in accordance with the invention.
Figure 2:
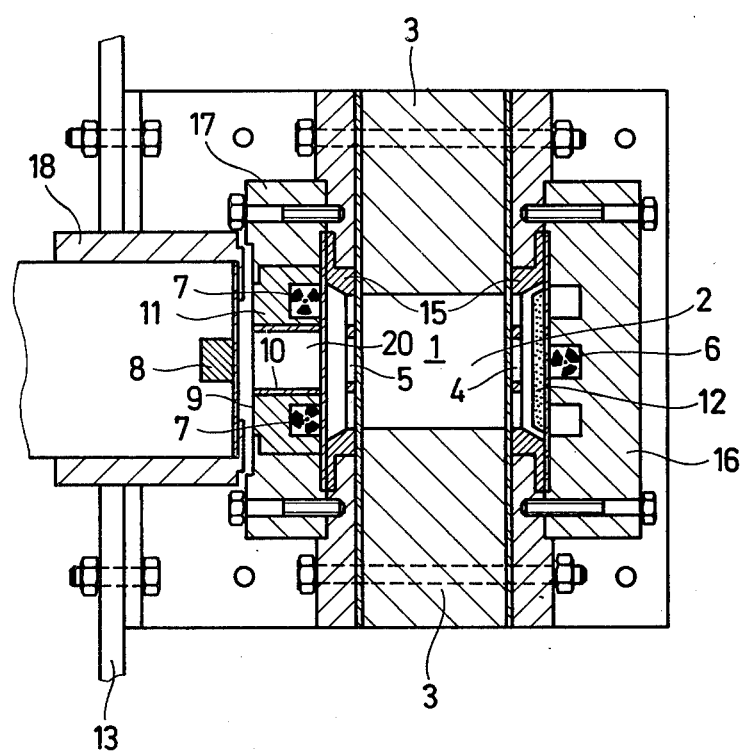

Referring to FIGS. 1 and 2, measuring chamber 1 includes a slurry channel 2 which can be varied in thickness by changing spacers 3 and thus can be optimized for the respective slurry composition. In slurry channel 2, on opposite sides thereof, the walls of measuring chamber 1 are equipped with measuring windows 4 and 5 required for X-ray fluorescence analysis processes. Windows 4 and 5 are made of 300 $\mu$m thick Hostaphan (terephthalate) film such as that manufactured by Hoechst AG. Supporting inserts 15 support windows 4 and 5 and prevent them from possible expansion or flapping during the analysis process.

A first source of primary radioactive radiation in the form of a point source 6 and a target 12 are mounted by a holder 16 behind window 4. A detector 8 is provided behind window 5 and a collimator, shown generally at 9, is disposed between detector 8 and window 5. Collimator 9 is located in a mount 17 and comprises a sleeve 10 surrounded by a shield 11. Mount 17 contains a flange which mates with shield 11. Sleeve 10 defines a passage 20 between detector 8 and window 5. An annular source 7 of radioactive radiation is enclosed by shield 11. Annular source 7 may either comprise a single source having the shape of an annulus or a plurality of sources disposed around passage 20. Both sources 6 and 7 can comprise $Co^{57}$.

As can be seen from FIGS. 1 and 2, point source 6, target 12, windows 4 and 5, collimator 9, source 7 and detector 8 are laterally aligned with each other.

Detector 8 is premanently fixed in a protective sleeve 18 and is screwed to an adjustment device (Fa. ALZ-METALL, Germany). Thus it is possible to very precisely and, importantly, reproducibly set the geometry of detector 8 with respect to measuring chamber 1.

Detector 8 is preferably an intrinsic germanium planar detector, such as that made by PGT (Princton Gamma-Tech., Wiesbaden, German). A 30 liter coolant container which operates with liquid nitrogen is provided for cooling detector 8. A safety device automatically switches off the high voltage if the cooling level is too low. There is thus no danger of destruction of detector 8 as a result of cooling system malfunction. By doubling the container volume, the replenishing intervals for liquid nitrogen are extended to about 20 days.

Measuring chamber 1 is permanently mounted in the measuring system by means of screw connections 13. Additionally provided seating pins (not shown) assure an accurate seat which can be reproduced at any time. Moreover, all individual components are manufactured to fit. Thus, there exists no danger of changes in geometry due to installation work.

The target material employed for Pb determination is 70 weight % mercury oxide encased in resin. The reason for the selection of mercury as the target material is the energy position of its X-ray lines.

Shield 11 is comprised of 75 weight % metallic tungsten powder embedded in resin and protects detector 8 against the primary radiation of annular source 7. Tungsten is selected as the shielding material because, next to lead, it has the most favorable attenuation characteristics. For the purpose of attenuating the tungsten inherent X-ray lines, shield 11 may be provided with a silver foil in the direction toward the radiation channel or detector 8. Sleeve 10 may be made from Sn, Cd, or Ag.

In operation, point source 6 emits primary radiation. Part of this primary radiation excites target 12 to emit X-ray radiation. Another part of this primary radiation causes the slurry contents in measuring chamber 1 to emit X-ray radiation. The element in the slurry to be analyzed, which in the present case is Pb, is thus caused to emit radiation. Primary radition from point source 6, target radiation, and element specific X-ray radiation excited by point source 6 are transmitted through the slurry and are measured by detector 8. The yield of element (Pb) specific X-ray radiation resulting from point source 6, however, is very low and not sufficient for determination of the element content. In accordance with the present invention annular source 7 is utilized in addition to point source 6 to realize a better yield of elemental X-ray radiation from the slurry contents. In fact a greater portion of the slurry elemental X-ray radiation is generated by annular source 7 on the side of detector 8. With this geometery, transmission as well as reflection are utilized in one measuring device.

Detector 8 converts the primary radiation, the target radiation and the X-ray radiation, as attentuated or reflected, respectively, by the slurry in measuring chamber 1 to electrical pulses. After preamplification and major amplification these pulses are received by a multichannel analyzer. The analyzer feeds the integrals of the spectral regions of interest for the evaluation (see FIGS. 3 and 4) via an interface to a programmable computer.

The theoretical basis for the invention is discussed below.

With the use of the X-ray K lines, the following formula can be set up for the measurement of the X-ray radiation of the element to be analyzed:

$$\tau_f = K_f \cdot \delta_p \cdot C_p \cdot \exp(X) \cdot \left[ \frac{E_2(X)}{H} - \frac{E_2(y)}{H+d} \right] \quad (1)$$

where:

$\tau_f$ = X-ray radiation of the element to be analyzed.
$K_f$ = geometry factor as well as the yield of characteristic X-ray radiation of the desired element;
$\delta_p$ = sample density (g/ccm);
$C_p$ = weight concentration of the desired element in the sample;
H = distance between detector and sample;
d = thickness of the sample;

$$X = \bar{\mu}_p \rho_p H, \quad y = X + \mu_p \rho_p d$$

$$\bar{\mu}_p = \mu_{oP} + \mu_{fP}$$

$\mu_{oP}$ = mass absorption coefficient of the sample for the primary radiation;
$\mu_{fP}$ = mass absorption coefficient of the sample for the elemental X-ray radiation; and
$E_2$ = exponential integral function of the general form $$E_2(x) = \int_\lambda^\infty \frac{e^{-tx}}{t^2} dt$$

The primary target radiation intensities $\tau_{T\phi}$ and $\tau_{T1}$, respectively, attenuated by the slurry, and measured by detector 8, can be expressed similarly to (1).

$$\tau_{T\phi} = K_{To} \cdot \exp(-\mu_{oP} \rho_p d) \quad (2)$$

$$\tau_{T1} = K_{T1} \cdot \exp(-\mu_{iP} \rho_p d) \quad (3)$$

$K_{T\phi}$, $K_{T1}$ are constants.

The selection of the corresponding sample thickness can bring the reduction of the second member of equation (1) to zero. Under this condition equation (1) is modified as follows:

$$\tau_f = K_f C_p \rho_p (A\phi + A_1 \cdot X) \quad (4)$$

$A_\phi A_1$ are constants.

The product $C_p \cdot \delta_p$ in this equation can be expressed as follows for the transmission values $\tau_{T\phi}$, $\tau_{T1}$ measured for the primary and target radiation:

C = concentration of the wanted element in the solid R,
$a_1$, $a_2\bar{\alpha}$, $\bar{\beta}$, $\bar{\gamma}$ = constants
Low = $\ln(\tau_{Tow}/\tau_{T\phi})$; $L_1W = \ln(\tau_{T1w}/\tau_{T1})$
$\tau_{T\phi}W$, $\tau_{T1}W$ = constants $$C_p \cdot \rho_p = \frac{C}{C-R} \cdot (a_1 \cdot L\phi W + a_2 \cdot L1W) \quad (5)$$

"X" is calculated in a similar manner:

$$X = \bar{\alpha} + \bar{\beta} \cdot L\phi W + \bar{\gamma} \cdot L1W \quad (6)$$

For the determination of C the formulas (4), (5), (6) are mathematically solved.

The lead content in total recoveries varies in a range from about 0.1% to 0.6% with a zinc content in the range from 0.5% to 0.3% and a slurry density of about 1.175 g/ccm.

A series of slurries were examined. All combinations of slurry densities (g/ccm) of 1.10, 1.15, 1.175, 1.20, 1.225 with lead concentrations in the solid material of 0.05, 0.1, 0.2 0.25, 0.3, 0.4, 0.5, 0.7 and 1% were covered. The zinc concentration was 0.2% in all samples. The samples are used to determine all constants mentioned above.

The excitation of X-ray lines of lead was effected by means of 122 KeV gamma energy from the approximately 0.5 MCi strong $Co^{57}$ annular source 7 (reflection geometry) and from the $Co^{57}$ point source 6 of the same strength (transmission geometry). Target 12 was mercury oxide cast in resin. As noted above, the selection of mercury is based on the energy position of its X-ray lines. The K-alpha $l$ line (70.82 KeV) of mercury lies near enough to the lead K lines to assure meeting the condition $\mu_f p \mu_1 p$=constant. However, this mercury line can nevertheless be measured separately from the lead lines with a detector 8 having good resolution. The thickness of target 12 was set so that the intensities of primary radiation (122 KeV) and target radiation (70.82 KeV) measured at a zero sample were approximately equal. This permitted measurements of both lines with a similar statistical error.

Figure 3:
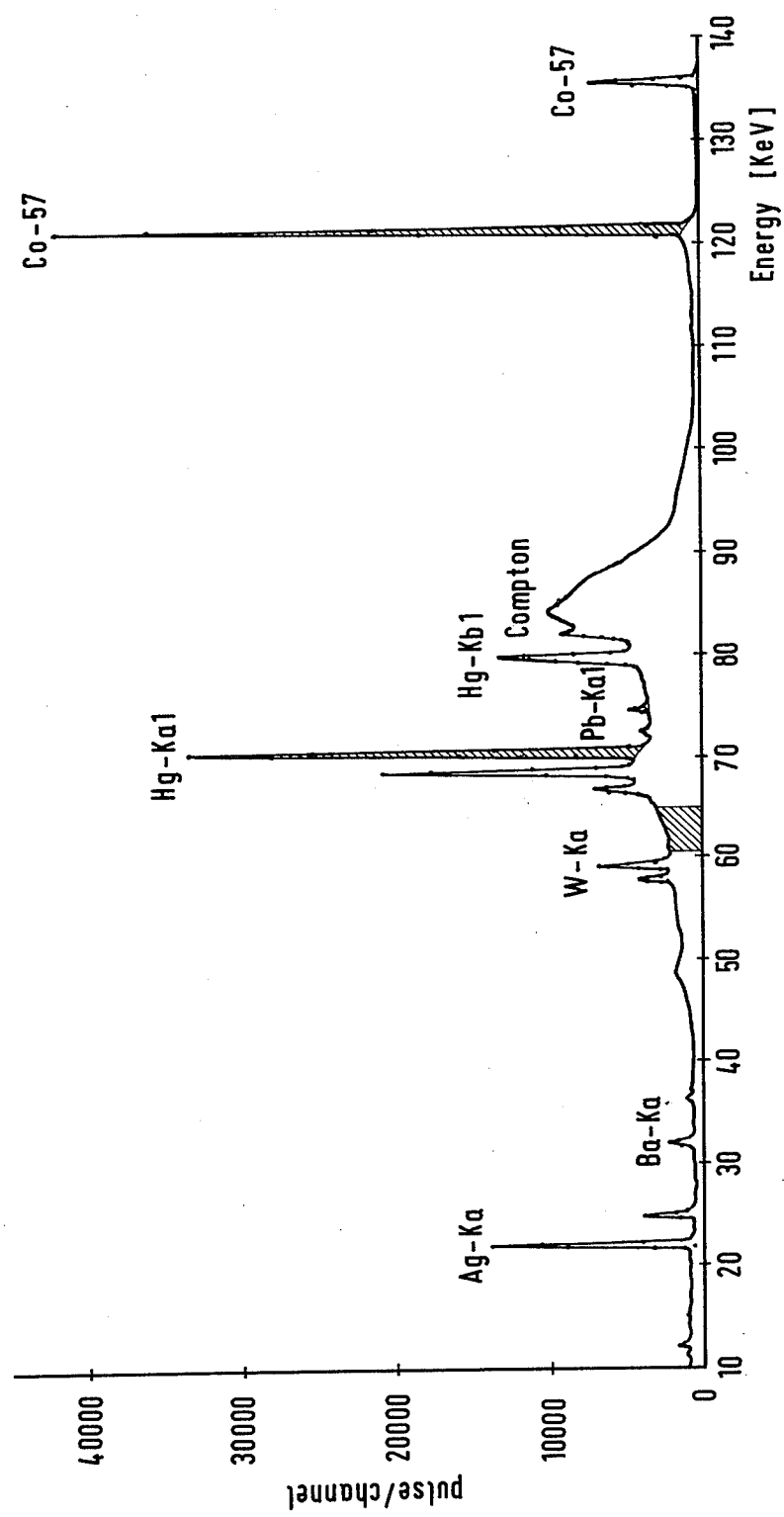
FIG. 3 shows an X-ray fluorescence spectrum of a slurry containing lead, produced by employing apparatus in accordance with the invention.
Figure 4:
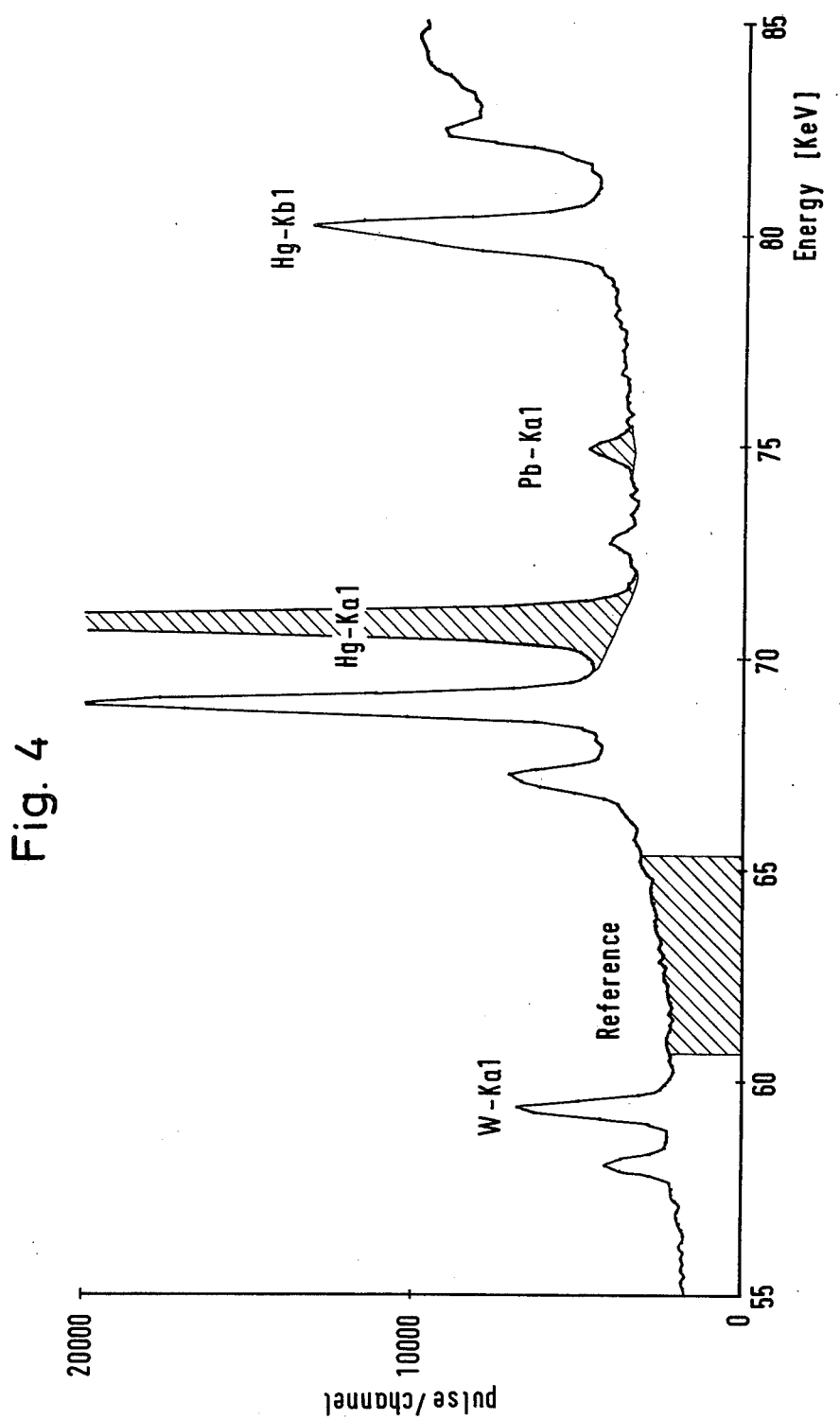
FIG. 4 is an enlarged view of a portion of the spectrum of FIG. 3.

FIG. 3 shows an X-ray fluorescence analysis spectrum for a particular determination (0.5 weight % Tb) in accordance with the above. FIG. 4 is an enlarged view of the spectrum of FIG. 3 from 55 to 85 KeV.

The various peaks in FIGS. 3 and 4 represent the regions of interest in the spectrum caused by excitation of the slurry. The net peak area for Hg-K alpha 1 and Pb-K alpha 1 are shown by the cross-hatching under their respective peaks. Background or reference radiation is also shown by cross-hatching. For a calculation of the net peak areas, a linear background subtraction was made. For this purpose the backgrounds from several channels to the left and right of the respective peak were calculated.

Figure 5:
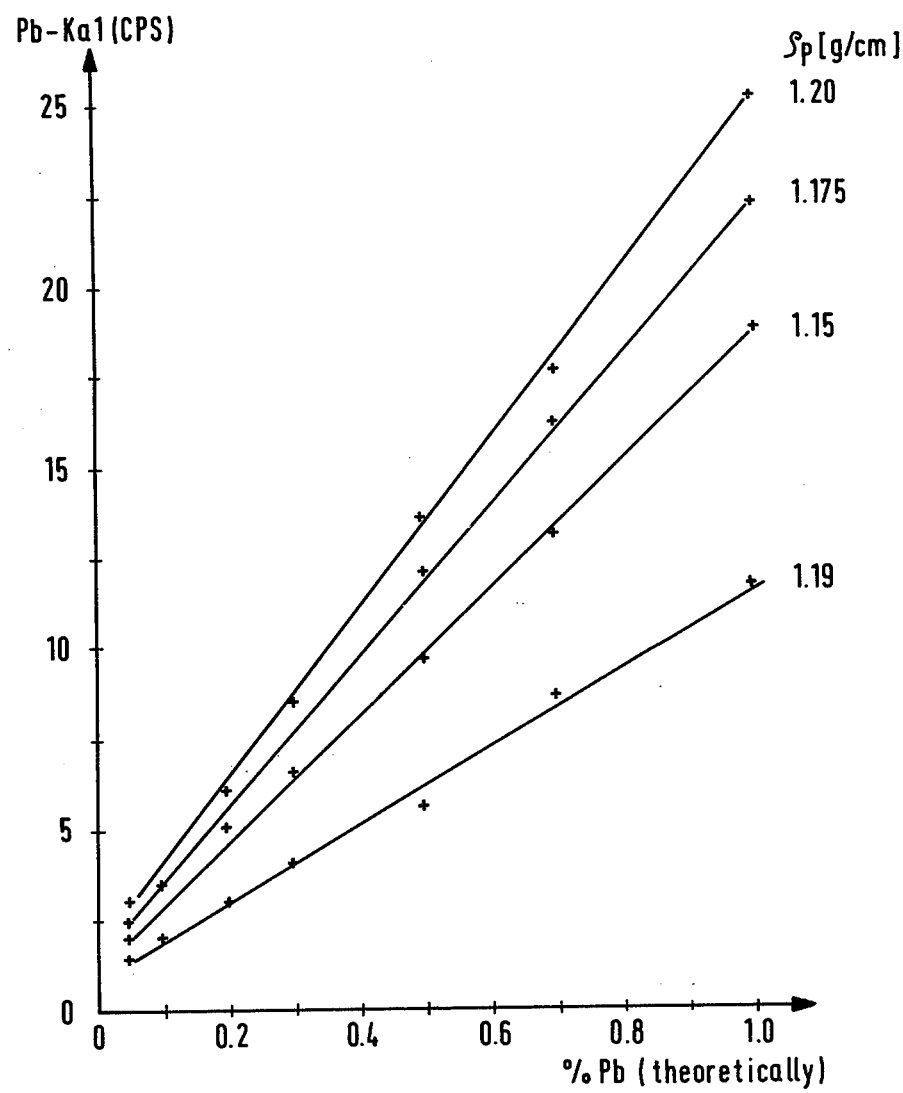
FIG. 5 is a graph of experimental results obtained by employing apparatus in accordance with the present invention and showing the variation of lead K-alpha 1 X-ray lines for varying concentrations of lead in the solid material and varying slurry densities.

FIG. 5 graphically shows the results of an experiment in which the intensity of the lead K-alpha 1 line (vertical axis) was measured for different concentrations of lead in the solid material (horizontal axis) and for different slurry densities (solid lines). As can be seen from FIG. 5, the intensity of the lead K-alpha 1 lines for any given concentrating of lead in the slurry depends on the density of the slurry. Thus, FIG. 5 clearly shows that the density influence must be eliminated in order to perform a valid quantitative analysis for determination of the Pb concentration.

Figure 6:
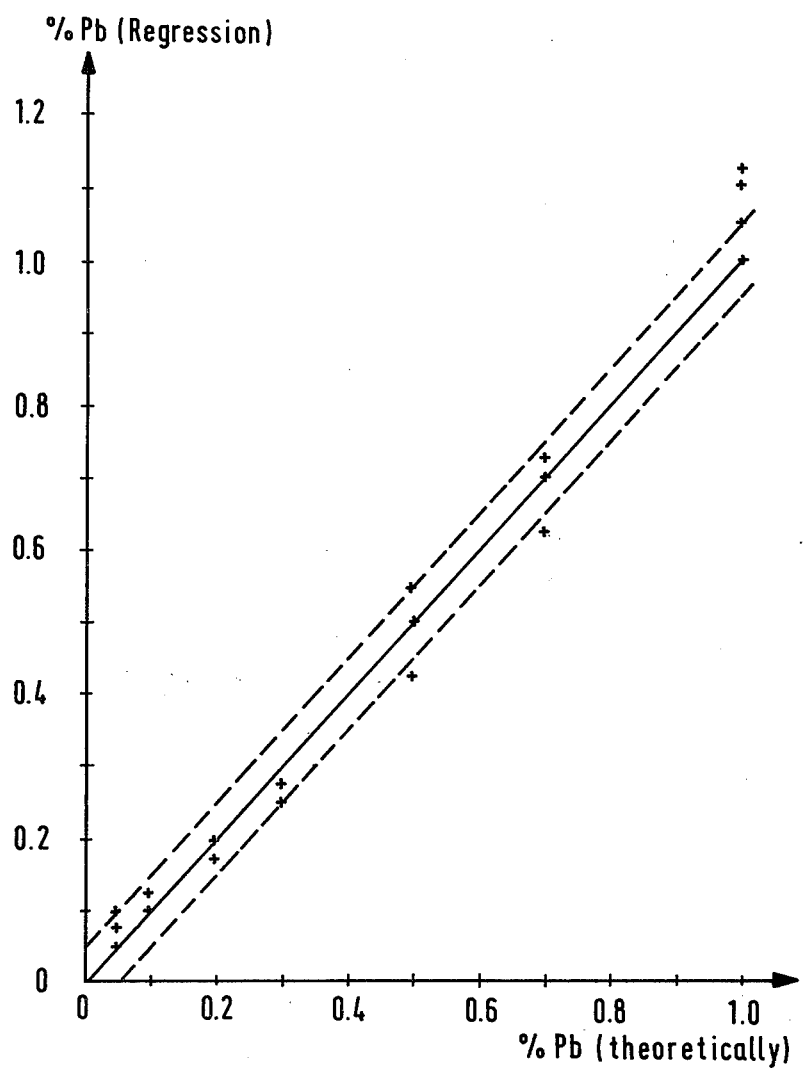
FIG. 6 is a graph of a regression analysis correlating the known lead concentration of slurries with that experimentally obtained by employing apparatus in accordance with the invention.

FIG. 6 shows the results of a first regression analysis made with the aid of measured values from 28 different slurries. The measured concentrations of lead are compared with the theoretical (i.e. known) concentrations of lead in the slurries. The interrupted lines in FIG. 6 delimit a region of four standard deviations (+or−two standard from the regression line). As can be seen, the coincidence between the experimental results and the known concentrations is good, which is also confirmed by the chi square value of about 45.3.

It must here be considered that malfunction due to interference was noted during the first series of measurements, explained in part by the electronic system employed and in part by inhomogeneities in the slurry. Changes made to the stirring mechanism noticeably improved the thorough mixing of the slurry.

It will be understood that various changes in the details, materials and steps which have been described herein to explain the nature of the invention may be made by those skilled in the art within the principle and scope of the invention as expressed in the appended claims.

What is claimed is:

1. In an apparatus for the continuous measurement by X-ray fluorescence analysis of the elemental contents of a slurry independent of the slurry density and slurry composition comprising: a measuring chamber having a slurry flow channel, a first measuring window provided at one side of the channel and a second measuring window provided at the other side of the channel, a detector disposed behind the first measuring window, a first source of primary radiation and a target disposed behind the second measuring window, the target being disposed between the second measuring window and the first source wherein the first source excites the target to emit target radiation and excites the slurry contents to emit X-ray radiation, and the primary radiation from the first source, the target radiation, and the excited X-ray are transmitted to and detected by the detector, the improvement comprising:

collimator means forming an open passage between said detector and said first measuring window, and an annular source of primary radiation for irradiating the slurry contents to excite additional X-ray radiation therefrom located between said detector and said first measuring window and about said open passage, wherein said collimator means collimates the primary radiation, target radiation and X-ray radiation excited by said first source and said annular source of primary radiation.

2. An apparatus as defined in claim 1, wherein said annular source comprises a plurality of individual sources disposed about said open passage.

3. An apparatus as defined in claim 1, wherein said annular source comprises a single source having the shape of an annulus.

4. An apparatus as defined in claim 1, 2 or 3 wherein said collimator means comprises a resin mass which is embedded with tungsten and a sleeve which is enclosed by the resin mass, and wherein said annular source is held in said resin mass.

5. An apparatus as defined in claim 4, wherein said sleeve comprises a material selected from the group consisting of Sn, Cd or Ag.

6. An apparatus as defined in claim 2, wherein said target is made of a resin mass with HgO bound therein.

* * * * *

UNITED STATES PATENT AND TRADEMARK OFFICE
CERTIFICATE OF CORRECTION

PATENT NO. : 4,450,576
DATED : May 22, 1984
INVENTOR(S) : Andrzej Lubecki et al

It is certified that error appears in the above-identified patent and that said Letters Patent is hereby corrected as shown below:

Please change the Assignee to read:

— Kernforschungszentrum Karlsruhe Gesellschaft mit beschrankter Haftung, Karlsruhe, Federal Republic of Germany —.

Signed and Sealed this

Sixteenth Day of October 1984

[SEAL]

*Attest:*

*Attesting Officer*

GERALD J. MOSSINGHOFF

*Commissioner of Patents and Trademarks*